United States Patent
Clark et al.

[11] Patent Number: 5,891,899
[45] Date of Patent: Apr. 6, 1999

[54] PHARMACEUTICAL XANTHENE COMPOUNDS

[75] Inventors: Barry Peter Clark, Lower Froyle; John Richard Harris, Guildford, both of England

[73] Assignee: Eli Lilly and Company Limited, Basingstoke, England

[21] Appl. No.: 990,253

[22] Filed: Dec. 15, 1997

[30] Foreign Application Priority Data

Dec. 17, 1996 [GB] United Kingdom ............ 9626151

[51] Int. Cl.⁶ .................. C07D 311/82; A61K 31/35
[52] U.S. Cl. .................. 514/383; 514/437; 514/454; 548/253; 544/26; 544/388
[58] Field of Search .................. 514/383, 437, 514/454; 544/26, 388; 548/253

[56] References Cited

FOREIGN PATENT DOCUMENTS

WO 95/15941  6/1995  WIPO .
WO 97/21715  6/1997  WIPO .

Primary Examiner—Robert Gerstl
Attorney, Agent, or Firm—Martin A. Hay

[57] ABSTRACT

A pharmaceutical compound of the formula:

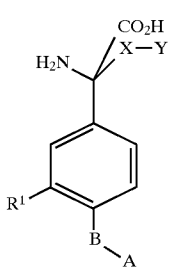

in which A is carboxy, tetrazolyl, $-SO_2H$, $-SO_3H$, $-OSO_3H$, $-CONHOH$, or $-P(OH)OR'$, $-PO(OH)OR'$, $-OPO(OH)OR'$ B is a bond, $C_{1-6}$ alkylene or $C_{2-6}$ alkenylene, $R^1$ is hydrogen, hydroxyl, halo or group of the formula A—B—, X is $C_{1-6}$ alkylene, $C_{2-6}$ alkenylene, $C_{2-6}$ alkynylene or $C_{1-6}$ alkylene linked through —O—, —S— or —NR"— to Y, where R" is hydrogen or $C_{1-6}$ alkyl, and Y is (1)

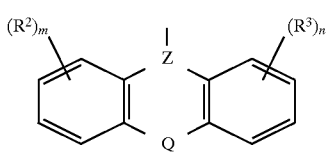

where p is and Z is

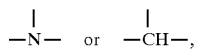

or (2)

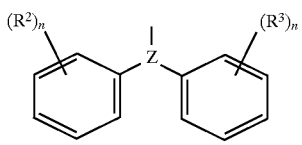

and salts and esters thereof.

10 Claims, No Drawings

PHARMACEUTICAL XANTHENE COMPOUNDS

This invention relates to novel compounds and their use as pharmaceuticals.

It is well known that excitatory neurotransmission in the mammalian central nervous system is primarily mediated by the amino acid, L-glutamate, acting on ionotropic and metabotropic receptors, and compounds that modify neurotransmission by interaction with these receptors are of interest for their potential use in the treatment of disorders of the central nervous system.

The compounds of the invention are of the formula:

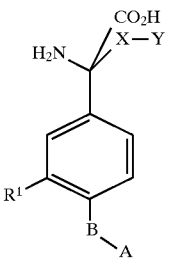

(I)

in which

A is carboxy, tetrazolyl, —$SO_2H$, —$SO_3H$, —$OSO_3H$, —CONHOH, or —P(OH)OR', —PO(OH)OR', —OPO(OH)OR' where R' is hydrogen, $C_{1-6}$ alkyl, $C_{2-6}$ alkenyl or optionally substituted phenyl-$C_{1-6}$ alkyl, B is a bond, $C_{1-6}$ alkylene or $C_{2-6}$ alkenylene, $R^1$ is hydrogen, hydroxyl, halo or group of the formula A—B—, X is $C_{1-6}$ alkylene, $C_{2-6}$ alkenylene, $C_{2-6}$ alkynylene or $C_{1-6}$ alkylene linked through —O—, —S— or —NR''— to Y, where R'' is hydrogen or $C_{1-6}$ alkyl, and Y is (1)

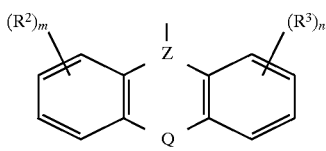

in which $R^2$ and $R^3$ are each halo, nitro, nitrile, $C_{1-6}$ alkyl, $C_{2-6}$ alkenyl, $C_{2-6}$ alkynyl or optionally substituted phenyl, m and n are each 0 to 3, Q is —O—, —S—, —SO—, —$SO_2$—, —CH=CH—, —$(CH_2)_p$—, —CONR'''— or —NR'''CO—, where p is 0 to 3 and R''' is hydrogen or $C_{1-6}$ alkyl, and Z is

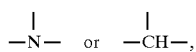

or (2)

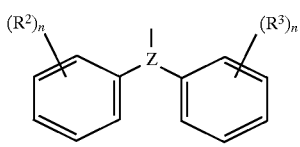

in which $R^2$, $R^3$, m, n and Z are as defined above;

provided that when Z is

X is $C_{1-6}$ alkylene, $C_{2-6}$ alkenylene or $C_{2-6}$ alkynylene; and salts and esters thereof.

The compounds of the invention have been found to be active in tests indicative of their use in the treatment of diseases of the central nervous system such as neurological diseases, for example, neurodegenerative diseases, and as antipsychotic, anticonvulsant, analgesic and anti-emetic agents.

In the above general formula, a $C_{1-6}$ alkyl group can be straight or branched chain, such as, for example, methyl, ethyl, propyl, isopropyl, butyl and isobutyl, and is preferably methyl or ethyl. A $C_{2-6}$ alkenyl group includes, for example, vinyl, prop-2-enyl, but-3-enyl, pent-4-enyl and isopropenyl, and an alkenyl group can contain more than one double bond and, in addition, one or more triple bonds. A preferred alkenyl group is of the formula R—CH=CH— where R is $C_{1-4}$ alkyl.

A halo substituent group can be fluoro, chloro, bromo or iodo, and is preferably fluoro or chloro.

In the above Formula (I), an optionally substituted phenyl is optionally substituted with, for example, one or more substituents, preferably 1 to 3 substituents, selected from $C_{1-4}$ alkyl, especially methyl, $C_{1-4}$ alkoxy, especially methoxy and ethoxy, carboxy, hydroxy, cyano, halo, especially bromo, chloro and fluoro, trifluoromethyl, nitro, amino, $C_{1-4}$ acylamino and $C_{1-4}$ alkylthio. When substituted, a phenyl group is preferably substituted by one to three substituents. An optionally substituted phenyl-$C_{1-6}$ alkyl group is one such group linked through an alkylene chain, for example, phenyl—$(CH_2)_x$—where x is 1 to 6, and a most preferred example is benzyl.

When B or X is $C_{1-6}$ alkylene it is preferably of the formula —$(CH_2)_y$—where y is 1 to 6, preferably 1 or 2. The alkylene chain can, however, be branched with alkyl groups, for example, methyl. A $C_{2-6}$ alkenylene is a bivalent $C_{2-6}$ alkenyl group preferably of the formula —$(CH_2)_x$(CH=CH)$(CH_2)_y$—where x is 0 to 2 and y is 1 or 2. A $C_{2-6}$ alkynylene group is a bivalent $C_{2-6}$ alkynyl group preferably of the formula —$(CH_2)_x$-(C≡C).$(CH_2)_y$—where x and y are each 1 or 2.

In preferred compounds the value of Y is as defined in (1) above.

It is preferred that A is carboxy or tetrazolyl or phosphonyl, and that B is $C_{1-6}$ alkylene preferably —$CH_2$—, or a bond. The group X is preferably $C_{1-6}$ alkylene, especially —$CH_2$— or —$CH_2CH_2$—, and Y is preferably of the formula:

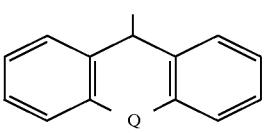

A preferred group of compounds of formula (I) is one in which A is carboxy, B is a bond, X is —$CH_2$—, $R^1$ is OH or H and Y is

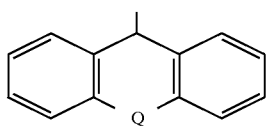

and Q is —O— or —S—.

It will be understood that salts of the compounds of the invention can be prepared, and such salts are included in the invention. They can be any of the well known base or acid addition salts. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium and sodium salt forms are particularly preferred.

Acid addition salts are preferably the pharmaceutically-acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, fumaric, malic, tartaric, citric, salicylic or o-acetoxybenzoic acids, or organic sulphonic acids, methane sulphonic, 2-hydroxyethane sulphonic, toluene-p-sulphonic or naphthalene-2-sulphonic acids.

In addition to pharmaceutically-acceptable salts, other salts are included in the invention. They may serve as intermediates in the purification of compounds or in the preparation of other, for example pharmaceutically-acceptable salts, or are useful for identification, characterisation or purification.

The compounds can also be utilised in ester form, such esters being aliphatic or aromatic, such as, for example, alkyl and phenolic esters. The most preferred esters are alkyl esters derived from $C_{1-4}$ alkanols, especially methyl and ethyl esters.

It will be appreciated that the compounds of the invention contain one or more asymmetric carbon atoms, and this gives rise to enantiomers. The compounds can be prepared as racemates or as enantiomers, and individual enantiomers can be isolated from racemates by conventional techniques if so desired.

The invention also includes a process for producing a compound of the invention, which comprises hydrolysing:
1) a compound of the formula:

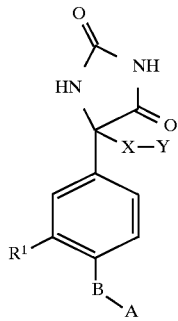

2) a compound of the formula:

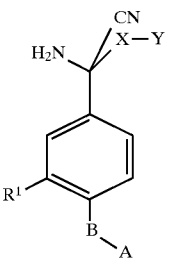

With regard to process variant (1), this reaction is preferably carried out in a solvent such as, for example, water, at an elevated temperature of from 50° C. to 200° C., and in the presence of an acid or base such as, for example, hydrochloric acid or sodium hydroxide. The intermediate compound of formula (II) can be prepared by reacting a compound of formula:

(IV)

with potassium cyanide and ammonium carbonate in aqueous ethanol under the conditions of the Bucherer-Bergs reaction, at a temperature of, for example, 30° C. to 120° C.

Compounds of formula (IV) can be synthesised by a number of routes, for example, by heating a compound of formula:

(V)

where

X' is an appropriate radical which, with the addition of a carbon atom, gives X, which in turn can be prepared by reaction of a compound of formula:

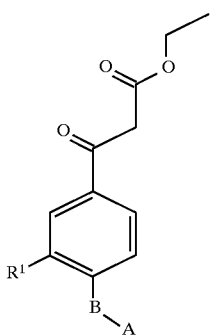

(VI)

with a reagent of the formula Y—X'—L where
L is a leaving group such as, for example, bromro.
Alternatively, the compound of formula (IV) can be prepared direct from the benzoyl halide:

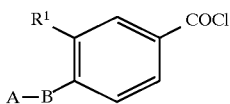

the source of compound (VI) above, by reaction with the iodide, Y—X—I, under the conditions of the Knochel coupling reaction.

The novel intermediates of formula (II) and (IV) are included as part of the present invention.

As mentioned above, the compounds of the invention have pharmaceutical activity. They have been shown to possess affinity for metabotropic glutamate receptors.

Excitatory amino acid or glutamate receptors are subdivided into two types, ionotropic and metabotropic. Ionotropic glutamate receptors are intrinsic ligand gated ion channels that are composed of multiple subunit proteins forming multimeric complexes. Ionotropic glutamate receptors are selectively activated by the agonists N-methyl-D-aspartate, AMPA, and kainate.

Metabotropic glutamate receptors are a family of G-protein coupled receptors with novel molecular structure that is coupled either to an increase in phosphoinositide (PI) hydrolysis or to a decrease in cAMP formation (Pin J-P. et al., 1995, Neuropharmacol. 34, 1–26).

Metabotropic glutamate receptors are subdivided into three major groups based on their pharmacology, amino acid sequence homology and the signal transduction pathway to which they couple. Group 1 comprises mGluR1 and mGluR5 which are coupled to phosphoinositide hydrolysis/calcium immobilisation, whereas group 2 (mGluR2 and 3) and group 3 (mGluR4, 6, 7 and 8) are negatively coupled to adenylate cyclase.

The compounds of the invention block the metabotropic glutamate receptor second messenger responses with IC50 values of less than 100 $\mu$M, including agonist-induced PI hydrolysis (Kingston A. E. et al., Neuropharmacology, 1995, 0034, N8, 887–894), and reversal of 1S,3R-ACPD-induced inhibition of forskolin-stimulated cAMP formation (Schoepp D. D., Johnson B. G., and Monn J. A., J. Neurochem. 58: 1184–1186, 1992). The affinity of the compounds for metabotropic glutamate receptors has also been demonstrated by the selective displacement of IS,3R-ACPD-sensitive $^3$H-glutamate binding to rat brain cell membranes, a test for metabotropic glutamate receptor activity described by Schoepp D. D. and True R. A. (Neuroscience Lett. 145: 100–104, 1992).

The activity at the receptors indicates potential for use in a wide range of of therapies. The additional activity at the mGluR5 receptors is potentially of especial therapeutic benefit.

Thus the compounds of the invention are indicated for use in the treatment of neurological disorders such as acute neurodegenerative diseases, for example stroke, cerebral ischemia and head and spinal cord trauma, and chronic neurodegenerative diseases such as for example Alzheimer's disease, Parkinson's disease, Amyotrophic lateral sclerosis, AIDS-induced dementia and Huntington's Chorea. The compounds are also indicated for use as antipsychotic, anticonvulsant, analgesic as for use in acute and chronic pain, and anti-emetic agents. They are also of potential use as anxiolytic and antidepressant agents.

The invention also includes a pharmaceutical composition comprising a pharmaceutically-acceptable diluent or carrier in association with a compound of Formula (I), or a pharmaceutically-acceptable salt thereof.

The compounds may be administered by various routes, for example, by the oral or rectal route, topically or parentally, for example by injection, and are usually employed in the form of a pharmaceutical composition. Such compositions form part of the present invention and are prepared in a manner well known in the pharmaceutical art and normally comprise at least one active compound in association with a pharmaceutically-acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. Where the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxbenzoate, talc, magnesium stearate and mineral oil. Compositions in injectable form may, as it is well known in the art, be formulated so as to provide quick, sustained or delayed release of the active ingredient after administration to the patient.

When the compositions are formulated in unit dosage form, it is preferred that each unit dosage form contains from 5 mg to 500 mg, for example, from 15 mg to 200 mg. The term 'unit dosage form' refers to physically discrete units suitable as unit dosages for human subjects and animals. Each unit contains a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range from 5 to 100 mg/kg. However, it will be understood that the amount administered will be determined by the physician in the light of the relevant circumstances, including the condition to be treated, the choice of compound to be administered and the chosen route of administration, and therefore the above dosage ranges are not intended to limit the scope of the invention in any way.

The invention is illustrated by the following Examples.

EXAMPLE 1

2-Amino-2-(4-carboxy-3-hydroxyphenyl)-3-(9H-xanthen-9-yl)propanoic acid i) 3-methoxy-4-methoxycarbonylbenzoyl chloride To a stirred suspension of 3-methoxy-4-methoxycarbonylbenzoic acid (4.1 g, 19.5 mmol) and oxalyl chloride (2.4 ml, 27.3 mmol) in dry dichloromethane (100 ml) was added 2 drops of dimethylformamide. After 3 h at room temperature the clear solution was evaporated to an oil. The oil was redissolved in dry dichloromethane and evaporated, this procedure was repeated to give 3-methoxy-4-methoxycarbonylbenzoyl chloride as an oil (100%) which was used immediately in the next step.

ii) Ethyl 3-methoxy-4-methoxycarbonylbenzoylacetate

To a solution of ethyl hydrogen malonate (4.38 g, 33.2 mmol) in dry tetrahydrofuran (100 ml) cooled under an atmosphere of nitrogen to −60° C. with efficient stirring was added a solution of n-butyllithium in hexane (2.5M, 26.5 ml) rapidly dropwise, allowing the temperature to rise to −10° C. during the addition. After stirring the resulting suspension for 15 min at −10° C. it was recooled to −70° C. and a solution of 3-methoxy-4-methoxycarbonylbenzoyl chloride (4.46 g, 19.5 mmol) in dry tetrahydrofuran (30 ml) added dropwise. After addition, the reaction mixture was allowed to warm to room temperature and after 1 h diluted with cold aqueous hydrochloric acid (2M, 35 ml) and ice. The mixture was extracted with diethyl ether (200 ml) and the extract washed twice with a saturated solution of sodium bicarbonate, water and a saturated solution of sodium chloride. The organic layer was dried over magnesium sulphate, filtered and evaporated. The residue was purified on flash silica eluting with dichloromethane to give ethyl 3-methoxy-4-methoxycarbonylbenzoylacetate as an oil.

iii) Ethyl 2-(9H-xanthen-9-yl)-2-(3-methoxy-4-methoxycarbonylbenzoyl)acetate

To a stirred solution of ethyl 3-methoxy-4-methoxycarbonylbenzoylacetate (4.1 g, 14.6 mmol) in a mixture of ethanol (30 ml) and acetic acid (30 ml) was added portionwise 9-hydroxyxanthene (3.2 g, 16.1 mmol). After stirring for 2 weeks at room temperature, the solution was concentrated in vacuo, diluted with water and extracted with dichloromethane (2×). The combined extracts were washed with a saturated solution of sodium bicarbonate, water and dried over magnesium sulphate. Filtration and evaporation gave ethyl 2-(9H-xanthen-9-yl)-2-(3-methoxy-4-methoxycarbonyl-benzoyl)acetate as an oil.

iv) Methyl 4-[2-(9H-xanthen-9-yl)acetyl]-2-methoxybenzoate

To a solution of ethyl 2-(9H-xanthen-9-yl)-2-(3-methoxy-4-methoxycarbonylbenzoyl)acetate (7.0 g, 14.6 mmol) in dimethylsulphoxide (40 ml) was added water (0.53 ml, 29.3 mmol). The solution was stirred under an atmosphere of nitrogen at reflux for 1.5 h before cooling and diluting with water. The mixture was extracted with dichloromethane (3×) and the combined extracts washed with water (5×) and a saturated solution of sodium chloride. The organic phase was dried over magnesium sulphate, filtered and evaporated to a yellow oil. Purification on flash silica eluting with dichloromethane-hexane (3:2 then 4:1) gave a solid which was crystallised from methanol to give methyl 4-[2-(9H-xanthen-9-yl)acetyl]-2-methoxybenzoate as a yellow solid.

v) 5-(9H-xanthen-9-ylmethyl)-5-(3-methoxy-4-methoxycarbonylphenyl)hydantoin

A mixture of methyl 4-[2-(9H-xanthen-9-yl)acetyl]-2-methoxybenzoate (2.65 g, 6.83 mmol), potassium cyanide (0.8 g, 12.3 mmol) and ammonium carbonate (2.4 g, 24.6 mmol) in ethanol-water (1:1, 20 ml) was heated in a teflon lined stainless steel sealed tube for 22 h at 85° C. with stirring. After cooling, the mixture was acidified with aqueous hydrochloric acid (5M) and extracted with ethyl acetate (4×). The combined extracts were dried over magnesium sulphate, filtered and evaporated to a gum. Purification on flash silica eluting with diethyl ether gave 5-(9H-xanthen-9-ylmethyl)-5-(3-methoxy-4-methoxycarbonylphenyl)hydantoin as a foam.

vi) 2-Amino-2-(4-carboxy-3-methoxyphenyl)-3-(9H-xanthen-9-yl)propanoic acid

A suspension of 5-(9H-xanthen-9-ylmethyl)-5-(3-methoxy-4-methoxycarbonylphenyl)hydantoin (1.04 g, 2.27 mmol) in aqueous sodium hydroxide (2M, 6.8 ml) was heated at 120° C. in a teflon lined stainless steel sealed tube for 3 days with stirring. After cooling, aqueous hydrochloric acid (5M, 3 ml) was added followed by purification on ion exchange (Dowex50×8–100 resin). The column was eluted sequentially with water, water-tetrahydrofuran (1:1), water and 10% pyridine in water. Fractions collected after the pyridine-water elution were combined, evaporated to dryness, redissolved in water and freeze-dried to give 2-amino-2-(4-carboxy-3-methoxyphenyl)-3-(9H-xanthen-9-yl)propanoic acid as a white powder.

vii) 2-Amino-2-(4-carboxy-3-hydroxyphenyl)-3-(9H-xanthen-9-yl)propanoic acid

To a suspension of 2-amino-2-(4-carboxy-3-methoxyphenyl)-3-(9H-xanthen-9-yl)propanoic acid (140 mg, 0.33 mmol) in dry dichloromethane (10 ml) was added a solution of boron tribromide in dichloromethane (1.0M, 0.7 ml). The resulting suspension was stirred at room temperature for 3 days, diluted with water and stirred a further 2 h. The dichloromethane layer was separated and the aqueous phase purified by ion exchange as described in Example 1 (vi). The water-tetrahydrofuran fractions were found to contain the desired product and were combined, evaporated and freeze-dried from water to give the title compound as a white powder, m.p. 191°–194° C.

EXAMPLE 2

2-Amino-2-(4-carboxy-2-methylphenyl)-3-(9H-xanthen-9-yl)propanoic acid i) 2-Methyl-4-bromobenzoyl chloride 2-Methyl-4-bromobenzoic acid (26.8 g) was treated with oxalyl chloride (16.3 ml) in dry dichloromethane (250 ml) and the product was isolated by the method described in Example 1 (i) to give 2-methyl-4-bromobenzoyl chloride as an oil.

ii) Ethyl 2-methyl-4-bromobenzoylacetate

2-Methyl-4-bromobenzoyl chloride (29.1 g, 0.13 mol) was treated with the dilithium salt of ethyl hydrogen malonate (28.0 g, 0.21 mol) and the product was isolated by the procedure described in Example 1 (ii). The crude product was purified on flash silica, eluting with dichloromethane-hexane (1:1 then 3:2) to give ethyl 2-methyl-4-bromobenzoylacetate as an oil.

iii) Ethyl 2-(4-bromo-2-methylbenzoyl)-2-(9H-xanthen-9-yl)acetate

A solution of ethyl 2-methyl-4-bromobenzoylacetate (18.5 g, 65.0 mmol) was heated at 60° C. with 9-hydroxyxanthene (14.2 g, 71.5 mmol) in ethanol-acetic acid (1:1, 200 ml) for 40 h. The product was isolated as in Example 1 (iii), except the aqueous phase was extracted with diethyl ether. The crude product was purified on flash silica eluting with hexane-dichloromethane (3:2 then 1:1) to give ethyl 2-(4-bromo-2-methylbenzoyl)-2-(9H-xanthen-9-yl)acetate as an oil.

iv) 1-(4-Bromo-2-methylphenyl)-2-(9H-xanthen-9-ylmethyl)ethanone

A solution of ethyl 2-(4-bromo-2-methylbenzoyl)-2-(9H-xanthen-9-yl)acetate (21.5 g, 46.0 mmol) in dimethylsulphoxide (100 ml) and water (1.6 ml) was refluxed for 1 h under an atmosphere of nitrogen. The reaction was worked up as in Example 1 (iv) and the crude product purified on flash silica eluting with hexane-dichloromethane (4:1 then 3:2) to give 1-(4-bromo-2-methylphenyl)-2-9H-xanthen-9-ylmethyl)ethanone as a solid.

v) 1-(4-Cyano-2-methylphenyl)-2-(9H-xanthen-9-ylmethyl)ethanone

A solution of cuprous cyanide (2.7 g, 30.5 mmol) and 1-(4-bromo-2-methylphenyl)-2-(9H-xanthen-9-ylmethyl)ethanone (10 g, 25.4 mmol) in dry dimethylformamide (80 ml) was heated to reflux under an atmosphere of nitrogen. After 24 h, further cuprous cyanide (2 g, 22.3 mmol) was added and reflux continued for another 20 h. The reaction mixture was cooled and a solution of ferric chloride (8.6 g, 52.9 mmol) in aqueous hydrochloric acid (2M, 200 ml) added. The resulting solution was diluted with water (400 ml) and extracted twice with diethyl ether, the combined extracts were washed with water (5×) and a saturated solution of sodium chloride. The organic phase was dried over magnesium sulphate, filtered and evaporated to a yellow oil. Purified on flash silica eluting with hexane-dichloromethane (4:1 then 3:2 then 1:1) to give 1-(4-cyano-2-methylphenyl)-2-(9H-xanthen-9-ylmethyl)ethanone as a yellow oil. Sample crystallised from hexane m.p. 138°–141° C.

vi) 5-(4-Cyano-2-methylphenyl)-5-(9H-xanthen-9-ylmethyl)hydantoin

A stirred mixture of 1-(4-cyano-2-methylphenyl)-2-(9H-xanthen-9-ylmethyl)ethanone (6.3 g, 18.6 mmol), potassium cyanide (2.2 g, 33.4 mmol) and ammonium carbonate (6.42 g, 66.9 mmol) in ethanol (9 ml) and water (9 ml) was heated at 85° C. for 2 days and then 100° C. for 3 days and finally 120° C. for 1 day in a teflon lined stainless steel sealed tube. The reaction was worked up as in Example 1 (v) to give a red oil. Purification on flash silica eluting with ethyl acetate-hexane (2:3 then 1:1 then 3:2) gave 5-(4-cyano-2-methylphenyl)-5-(9H-xanthen-9-ylmethyl)hydantoin as a pale yellow solid, m.p. 148°–152° C.

vii) 2-Amino-2-(4-carboxy-2-methylphenyl)-3-(9H-xanthen-9-yl)propanoic acid

A suspension of 5-(4-cyano-2-methylphenyl)-5-(9H-xanthen-9-ylmethyl)hydantoin (0.53 g, 1.30 mmol) in aqueous sodium hydroxide (2M, 3.9 ml) was heated at 150° C. for 3 days and the product isolated following the procedure described in Example 1 (vi) to give the title compound as a white powder, m.p. 215°–216° C.

EXAMPLE 3

2-Amino-2-(4-carboxyphenyl)-3-(9H-xanthen-9-ylmethyl)propanoic acid i) Ethyl 4-cyanobenzoylacetate The reaction was carried out by the procedure described in Example 1 (ii) from 4-cyanobenzoyl chloride (9.5 g) to give ethyl 4-cyanobenzoylacetate as a crystalline yellow solid from ethanol, m.p. 64° C.

ii) Ethyl 2-(4-cyanobenzoyl)-2-(9H-xanthen-9-yl)acetate

Ethyl 4-cyanobenzoyl acetate (6.7 g, 30.9 mmol) was added to a stirred solution of 9-hydroxyxanthene (6.1 g, 30.9 mmol) in ethanol (15 ml) and acetic acid (15 ml). The opaque solution became clear after 15 min and after 16 h at room temperature solid precipitated. The white solid was filtered then washed with water and dried in vacuo to give ethyl 2-(4-cyanobenzoyl)-2-(9H-xanthen-9-yl)acetate as a white solid, m.p. 141° C.

iii) 4-[2-(4H-benzopyran-4-yl)acetyl]benzonitrile
Method 1

2-(4-Cyanobenzoyl)-2-(9H-xanthen-9-yl)acetate (8.1 g, 20.4 mmol) was dissolved in dimethylsulfoxide (100 ml), water (0.74 ml) was added and the resulting solution heated at 190° C., under $N_2$ for 45 min. The cooled yellow solution was diluted with water and then extracted with ethyl acetate, washing with water then drying over magnesium sulphate, filtration and evaporation in vacuo gave 4-[2-(4 H-benzopyran-4-yl)acetyl]benzonitrile as a yellow solid, m.p. 111° C.
Method 2

A mixture of 9-iodomethyl-9H-xanthene (6.28 g, 19.49 mmol), zinc-copper couple (3.5 g) and N,N-dimethylacetamide (13.9 ml) in dry toluene (100 ml) was heated at 60° C. under an atmosphere of nitrogen for 3 hours with stirring. Tetrakis (triphenylphosphine) palladium(o) (0.52 g) was then added and heating continued at 60° C. for 5 minutes. The reaction mixture was cooled to room temperature and 4-cyanobenzoylchloride (3.55 g, 21.45 mmol) added and stirring continued overnight at room temperature. The reaction mixture was diluted with diethyl ether (200 ml), filtered through a pad of celite and the filtrate washed with an aqueous solution of sodium thiosulphate (10%, 300 ml) and a saturated solution of sodium chloride. The organic phase was dried over magnesium sulphate, filtered and evaporated to an oil. Purification on flash silica eluting with petroleum ether (40°–60° C.)-diethyl ether (4:1) was followed by further chromatography on flash silica eluting with dichloromethane to give 4-2[2-9H-xanthen-9-yl)acetyl]benzonitrile.

iv) 5-(4-Cyanophenyl)-5-(9H-xanthen-9-yl)hydantoin

The reaction of 4-[2-(4H-benzopyran-4-yl)acetyl]benzonitrile (6.4 g, 19.6 mmol), ammonium carbonate (6.6 g, 68.6 mmol) and potassium cyanide (1.90 g, 29.4 mmol) in ethanol-water (1:1, 20 ml) was carried out as described in Example (v) with additional heating at 100° C. for 3 days to give after work up and chromatography on flash silica eluting with ethyl acetate-hexane (3:2) 5-(4-cyanophenyl)-5-(9H-xanthen-9-yl)hydantoin.

v) 2-Amino-2-(4-carboxyphenyl)-3-(9H-xanthen-9-yl)propanoic acid

Hydrolysis of 2-amino-2-(4-carboxyphenyl)-3-(9H-xanthen-9-yl)propanoic acid (4.0 g, 0.01mol) with 50% NaOH (4.8 ml, 0.06 mol) diluted with water (20 ml) was by the procedure shown in Example 1 (vi) to give the title compound as a white powder.

EXAMPLE 4

2-Amino-2-(4-carboxyphenyl)-3-(9H-thioxanthen-9-yl)propanoic acid i) Ethyl 2-(4-cyanobenzoyl)-2-(9H-thioxanthen-9-yl)acetate Ethyl-4-cyanobenzoyl acetate (6 g, 28 mmol) and 9-hydroxy thioxanthene (6.6 g, 31 mmol) were mixed in acetic acid (50 ml) and ethanol (50 ml) using the procedure described in Example 3 (ii) to give ethyl 2-(4-cyanobenzoyl)-2-(9H-thioxanthen-9-yl)acetate as a pale yellow solid.

ii) 4-[2-(9H-thioxanthen-9-yl)acetyl]benzonitrile

A solution of ethyl 2-(4-cyanobenzoyl)-2-(9H-thioxanthen-9-yl)acetate (5 g, 12.0 mmol) in dimethylsulphoxide (50 ml) and water (0.45 ml) was reacted as described in Example 1 (iv) and the product was isolated in a similar manner except the extraction used diethyl ether to give 4-[2-(9H-thioxanthen-9-yl)acetyl]benzonitrile as a yellow oil which solidified on standing.

iii) 5-(4-Cyanophenyl)-5-(9H-thioxanthen-9-ylmethyl) hydantoin

Following the procedure described in Example (v) using 4-[2-(9H-thioxanthen-9-yl)acetyl]benzonitrile (3 g, 8.8 mmol), ammonium carbonate (3.1 g, 3.2 mmol) and potassium cyanide (1.03 g, 5.8 mmol) in ethanol-water (1:1, 15 ml) gave after work up a yellow solid. This was purified on flash silica eluting with dichloromethane and then ethyl acetate. The ethyl acetate fractions were combined and evaporated to a solid which was triturated with dichloromethane to give 5-(4-cyanophenyl)-5-(9H-thioxanthen-9-ylmethyl) hydantoin as a yellow solid.

iv) 2-Amino-2-(4-carboxyphenyl)-3-(9H-thioxanthen-9-yl)propanoic acid 5-(4-Cyanophenyl)-5-(9H-thioxanthen-9-ylmethyl) hydantoin (2.3 g, 5.5 mmol) was hydrolysed in aqueous sodium hydroxide (16.5 ml) following the procedure described in Example 1 (vi) for 72 h at 150° C. The cooled reaction mixture was then acidified with acetic acid, the resulting solid precipitate was filtered and washed with diethylether to give an off white solid. The solid was redissolved in aqueous sodium hydroxide (2M), filtered through a celite pad and acidified with acetic acid, filtered, washed with water, diethylether and finally methanol and then dried in vacuo to give the title compound as a white solid, m.p. 251° C.

EXAMPLE 5

2-Amino-3-(9H-xanthen-9-yl)-2-(4-phosphonophenyl)propanoic acid i) Ethyl 4-bromobenzoylacetate The reaction of 4-bromobenzoyl chloride (25.0 g, 0.11 mol) with the dilithium salt of ethyl monohydrogenmalonate (26.9 g, 0.2mol) was carried out by the procedure described in Example 1 (ii). The crude product was purified on flash silica eluting with dichloromethane to give ethyl 4-bromobenzoylacetate as an oil.

ii) Ethyl 2-(4-bromobenzoyl)-2-(9H-xanthen-9-yl)acetate

A solution of ethyl 4-bromobenzoylacetate (14.8 g, 0.05 mol) and 9-hydroxyxanthene (10.9 g, 0.06 mol) in ethanol-acetic acid (1:1, 150 ml) was stirred as described in Example 3 (ii) and a white solid collected. The filtrate was stirred a further 3 days and a second crop collected to give ethyl 2-(4-bromobenzoyl)-2-(9H-xanthen-9-yl)acetate.

iii) 1-(4-Bromophenyl)-2-(9H-xanthen-9-yl)ethanone

Ethyl 2-(4-bromobenzoyl)-2-(9H-xanthen-9-yl)acetate (10.0 g, 0.02 mol) was heated in a solution of dimethylsulphoxide (100 ml) and water (0.72 ml) following the procedure described in Example (iv) to give 1-(4-bromophenyl)-2-(9H-xanthen-9-yl)ethanone as a yellow solid.

iv) Diethyl 4-(9H-xanthen-9-ylmethylketo)benzenephosphonate

Triethylphosphite (7.2 g, 0.043 mol) was added dropwise to a solution of 1-(4-bromophenyl)-2-(9H-xanthen-9-yl)ethanone (6.8 g, 0.018 mol) and nickel (ii) bromide (0.2 g) in diphenylether (100 ml) stirred at a temperature of 160° C.

After addition, heated at 160° C. for 5 h, cooled and purified by vacuum elution through flash silica with dichloromethane followed by ethyl acetate-hexane (3:2). The ethyl acetate containing fractions were combined and evaporated to give diethyl 4-(9H-xanthen-9-ylmethylketo)benzenephosphonate as a yellow oil.

v) 5-(4-Diethylphosphonophenyl)-5-(9H-xanthen-9-ylmethyl)hydantoin

A mixture of diethyl 4-(9H-xanthen-9-ylmethylketo)benzenephosphonate (6.1g, 0.014 mol), potassium cyanide (1.64 g, 0.025 mol) and ammonium carbonate (4.84 g, 0.05 mol) in ethanol-water (1:1, 20 ml) was reacted as described in Example 1 (v). The ethyl acetate extract was concentrated in vacuo and filtered through a plug of flash silica under vacuum eluting with ethyl acetate to give after evaporation 5-(4-diethylphosphonophenyl)-5-(9H-xanthen-9-yl) hydantoin as a yellow solid.

vi) 2-Amino-3-(9H-xanthen-9-yl)-2-(4-diethylphosphonophenyl)propanoic acid 5-(4-Diethylphosphonophenyl)-5-(9H-xanthen-9-ylmethyl)hydantoin (1.0 g), 2.0 mmol) was reacted with aqueous sodium hydroxide (2M, 6 ml) in water (4 ml) following the procedure described in Example 1 (vi) to give 2-amino-3-(9H-xanthen-9-yl)-2-(4-diethylphosphonophenyl)propanoic acid as a white powder.

vii) 2-Amino-3-(9H-xanthen-9-yl)-2-(4-phosphonophenyl) propanoic acid

To a suspension of 2-amino-3-(9H-xanthen-9-yl)-2-(4-diethylphosphonophenyl)propanoic acid (114 mg, 0.25 mmol) in dry dichloromethane (10 ml) stirred under an atmosphere of nitrogen was added trimethylsilyl iodide (0.26 g, 1.29 mmol). The resulting solution was stirred at room temperature for 24 h and then further trimethylsilyl iodide (0.26 g, 1.29 ml) added. Stirring was continued for 5 h, the reaction mixture evaporated to dryness and redissolved in water. Ion exchange chromatography using the conditions described in Example 1 (vi) gave the title compound as a pale yellow powder.

EXAMPLE 6

2-Amino-2-[4-(1H-tetrazol-5-yl)phenyl]-3-(9H-xanthen-9-yl)propanoic acid i) 5-(9H-xanthen-9-ylmethyl)-5-[4-(1H-tetrazol-5-yl)phenyl]hydantoin A solution of 5-(4-cyanophenyl)-5-(9H-xanthen-9-yl) hydantoin (0.51 g, 1.3 mmol) in dimethylformamide (2 ml) was treated with tributyltin azide (0.86 g, 2.6 mmol) and heated with stirring at 120° C. overnight. Aqueous hydrochloric acid (5M, 0.55 ml) was added, the reaction mixture was cooled, diluted with water and extracted with ethyl acetate (5×). The combined extracts was washed once with water and a saturated solution of sodium chloride, dried over magnesium sulphate, filtered and evaporated. The residue was crystallised from dichloromethane to give 5-(9H-xanthen-9-ylmethyl)-5-[4- (1H-tetrazol-5-yl)phenyl] hydantoin as a white solid.

ii) 2-Amino-2-[4-(1H-tetrazol-5-yl)phenyl]-3-(9H-xanthen-9-yl)propanoic acid 5-(9H-xanthen-9-ylmethyl)-5-[4-(1H-tetrazol-5-yl) phenyl]hydantoin (3.2 g, 7.6 mmol) was heated with aqueous sodium hydroxide (2M, 23 ml) at 130° C. for 2 days following the procedure described in Example 1 (vi). The reaction mixture was acidified with aqueous hydrochloric acid and the product isolated by filtration to give the title compound as a white solid.

We claim:
1. A compound of the formula:

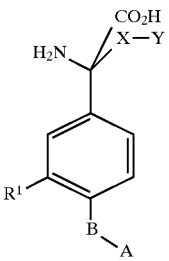

in which
A is carboxy, tetrazolyl, —SO$_2$H, —SO$_3$H, —OSO$_3$H, —CONHOH, or —P(OH)OR', —PO(OH)OR', —OPO(OH)OR' where R' is hydrogen, C$_{1-6}$ alkyl, C$_{2-6}$ alkenyl or optionally substituted phenyl-C$_{1-6}$ alkyl, B is a bond, C$_{1-6}$ alkylene or C$_{2-6}$ alkenylene, R$^1$ is hydrogen, hydroxyl, halo or group of the formula A—B—, X is C$_{1-6}$ alkylene, C$_{2-6}$ alkenylene, C$_{2-6}$ alkynylene or C$_{1-6}$ alkylene linked through —O—, —S— or —NR"— to Y, where R" is hydrogen or C$_{1-6}$ alkyl, and Y is (1)

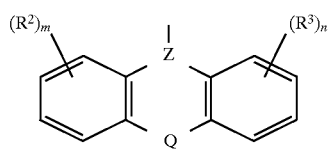

in which

R$^2$ and R$^3$ are each halo, nitro, nitrile, C$_{1-6}$ alkyl, C$_{2-6}$ alkenyl, C$_{2-6}$ alkynyl or optionally substituted phenyl, m and n are each 0 to 3, Q is —O—, —S—, —SO—, —SO$_2$—, —CH=CH—, —(CH$_2$)$_p$—, —CONR'''— or —NR''' CO—, where p is 0 to 3 and R''' is hydrogen or C$_{1-6}$ alkyl, and Z is

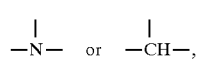

or (2)

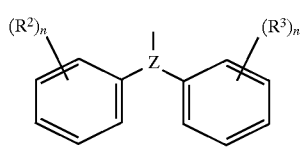

in which

R$^2$, R$_3$, n and Z are as defined above;

provided that when Z in (1) and (2) above is

X is C$_{1-6}$ alkylene, C$_{2-6}$ alkenylene or C$_{2-6}$ alkynylene; or a salt or ester thereof.

2. A compound according to claim 1 in which Y is (1).

3. A compound according to claim 2 in which A is carboxy, tetrazolyl or phosphonyl, and B is C$_{1-6}$ alkylene or a bond.

4. A pharmaceutical formulation comprising a compound of formula I as defined in claim 1, or a pharmaceutically-acceptable salt or ester thereof, together with a pharmaceutically-acceptable diluent or carrier therefor.

5. A method of treating an animal suffering from or susceptible to a disorder of the central nervous system, which comprises administering to said animal a compound of formula I according to claim 1, or a pharmaceutically acceptable salt or ester thereof.

6. A compound according to claim 3, in which B is —CH$_2$— or a bond.

7. A compound according to claim 2, in which X is C$_{1-6}$ alkylene and Y is of the formula:

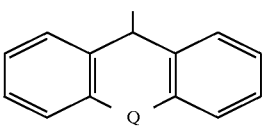

8. A compound according to claim 7, in which X is —CH$_2$— or —CH$_2$CH$_2$—.

9. A compound according to claim 8, in which A is carboxy, B is a bond, X is —CH$_2$—, R$^1$ is OH or H and Y is

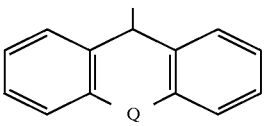

and Q is —O— or —S.

10. A method according to claim 5, in which the animal is a human.